US006528661B2

(12) United States Patent
Niddam et al.

(10) Patent No.: US 6,528,661 B2
(45) Date of Patent: Mar. 4, 2003

(54) **HYDROLYSIS OF [R(R*,R*)]-2-(4-FLUOROPHENYL)-β,δ-DIHYDROXY-5-(1-METHYLETHYL)-3-PHENYL-4-[(PHENYLAMINO) CARBONYL]-1H-PYRROLE-1-HEPTANOIC ACID ESTERS WITH CALCIUM HYDROXIDE**

(75) Inventors: Valerie Niddam, Even-Yeouda (IL); Ramy Lidor-Hadas, Kfar Saba (IL); Revital Lifshitz, Herzlia (IL); Eti Ishai, Netanya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/037,412

(22) Filed: Oct. 24, 2001

(65) Prior Publication Data

US 2002/0099224 A1 Jul. 25, 2002

Related U.S. Application Data

(60) Provisional application No. 60/326,529, filed on Oct. 1, 2001, provisional application No. 60/312,144, filed on Aug. 13, 2001, and provisional application No. 60/249,319, filed on Nov. 16, 2000.

(51) Int. Cl.$^7$ .................................................. C07F 3/04
(52) U.S. Cl. ..................................................... 548/537
(58) Field of Search ......................................... 548/537

(56) References Cited

U.S. PATENT DOCUMENTS

| 4,681,893 | A | 7/1987 | Roth |
| 5,003,080 | A | 3/1991 | Butler et al. |
| 5,097,045 | A | 3/1992 | Butler et al. |
| 5,124,482 | A | 6/1992 | Butler et al. |
| 5,149,837 | A | 9/1992 | Butler et al. |
| 5,216,174 | A | 6/1993 | Butler et al. |
| 5,245,047 | A | 9/1993 | Butler et al. |
| 5,273,995 | A | 12/1993 | Roth |
| 5,280,126 | A | 1/1994 | Butler et al. |
| 5,298,627 | A | 3/1994 | Butler et al. |
| 6,274,740 | B1 | 8/2001 | Lin et al. |

OTHER PUBLICATIONS

Brower, P.L. et al., "The Synthesis of (4R–cis)–1,1–Dimethylethyl 6–cyanomethyl–2,2–dimethyl–1,3–dioxane–4–acetate, a Key Intermediate for the Preparation of CI–981, a Highly Potent, Tissue Selective Inhibitor of HMG–CoA Reductase," Tet. Lett. 1992, 33, 2279–82.

Baumann, K.L. et al., "The Convergent Synthesis of CI–981, an Optically Active, Highly Potent, Tissue Selective Inhibitor of HMG–CoA Reductase," Tet. Lett. 1992, 33, 2283–84.

Roth, B.D. et al., "Inhibitors of Cholesterol Biosynthesis. 3. Tetrahydro–4–hydroxy–6–[2–(1H–pyrrol–1–yl]–2H–pyran–2–one Inhibitors of HMG–CoA Reductase. 2. Effects of Introducing Substituents at Positions Three and Four of the Pyrrole Nucleus," J. Med. Chem. 1991, 34, 357–66.

Kearney, A.S. et al., "The Interconversion Kinetics, Equilibrium, and Solubilities of the Lactone and Hydroxyacid Forms of the HMG–CoA Reductase Inhibitor, CI–981", Pharm. Res. 1993, 10, 1461–65.

*Primary Examiner*—Joseph K. McKane
*Assistant Examiner*—Rebecca Anderson
(74) *Attorney, Agent, or Firm*—Kenyon & Kenyon

(57) ABSTRACT

The present invention provides a process for preparing atorvastatin hemi-calcium from an atorvastatin ester derivative with calcium hydroxide. The process is conveniently incorporated into a process for preparing atorvastatin hemi-calcium from an acetonide protected, ester protected β,δ-dihydroxy heptanoic acid precursor compound by a first acid hydrolysis step followed by base hydrolysis with calcium hydroxide. The latter process may be performed as a one-pot process.

22 Claims, No Drawings

HYDROLYSIS OF [R(R*,R*)]-2-(4-FLUOROPHENYL)-β,δ-DIHYDROXY-5-(1-METHYLETHYL)-3-PHENYL-4-[(PHENYLAMINO) CARBONYL]-1H-PYRROLE-1-HEPTANOIC ACID ESTERS WITH CALCIUM HYDROXIDE

CROSS-REFERENCE TO RELATED APPLICATIONS

This invention claims the benefit under 35 U.S.C. 1.119(e) of provisional applications Serial No. 60/249,319, filed Nov. 16, 2000; No. 60/312,144, filed Aug. 13, 2001 and provisional application Serial No. 60/326,529, filed Oct. 1, 2001, which are incorporated herein by reference.

FIELD OF THE INVENTION

The present invention relates to compounds that suppress cholesterol biosynthesis in humans by competitively inhibiting 3-hydroxy-3-methyl-glutaryl-coenzyme A reductase and, more particularly, to processes for preparing pharmaceutically appropriate salts for oral administration of such compounds.

BACKGROUND OF THE INVENTION

[R(R*,R*)]-2-(4-fluorophenyl)-β,δ-dihydroxy-5-(1-methylethyl)-3-phenyl-4-[(phenylamino)carbonyl]-1H-pyrrole-1-heptanoic acid ("atorvastatin") is an inhibitor of cholesterol biosynthesis in humans. It is one of a class of drugs called statins. Statins suppress cholesterol biosynthesis by competitively inhibiting 3-hydroxy-3-methyl-glutaryl-coenzyme A reductase ("HMG-CoA reductase"). HMG-CoA reductase catalyzes the conversion of HMG-CoA to mevalonate, which is the rate determining step in the biosynthesis of cholesterol. Goodman and Gilman, *The Pharmacological Basis of Therapeutics* 841 (MacMillan Publ. Co.: New York 7th ed. 1985). Decreased production of cholesterol stimulates LDL receptor activity and consequently reduces the concentration of LDL particles in the bloodstream. Reducing LDL concentration in the bloodstream decreases the risk of coronary artery disease *J.A.M.A.* 1984, 251, 351–74.

Racemic trans-5-(4-fluorophenyl)-2-(1-methylethyl)-N,4-diphenyl-1-[2-tetrahydro-4-4-hydroxy-6-oxo-2H-pyran-2-yl)ethyl]-1H-pyrrole-carboxamide ("the racemic atorvastatin lactone") was reported to be a useful inhibitor of cholesterol biosynthesis in U.S. Pat. No. 4,681,893, in 1987. The racemic lactone was synthesized according to the chemical process summarized in Scheme 1.

Scheme 1

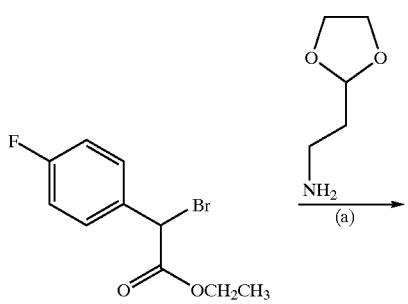

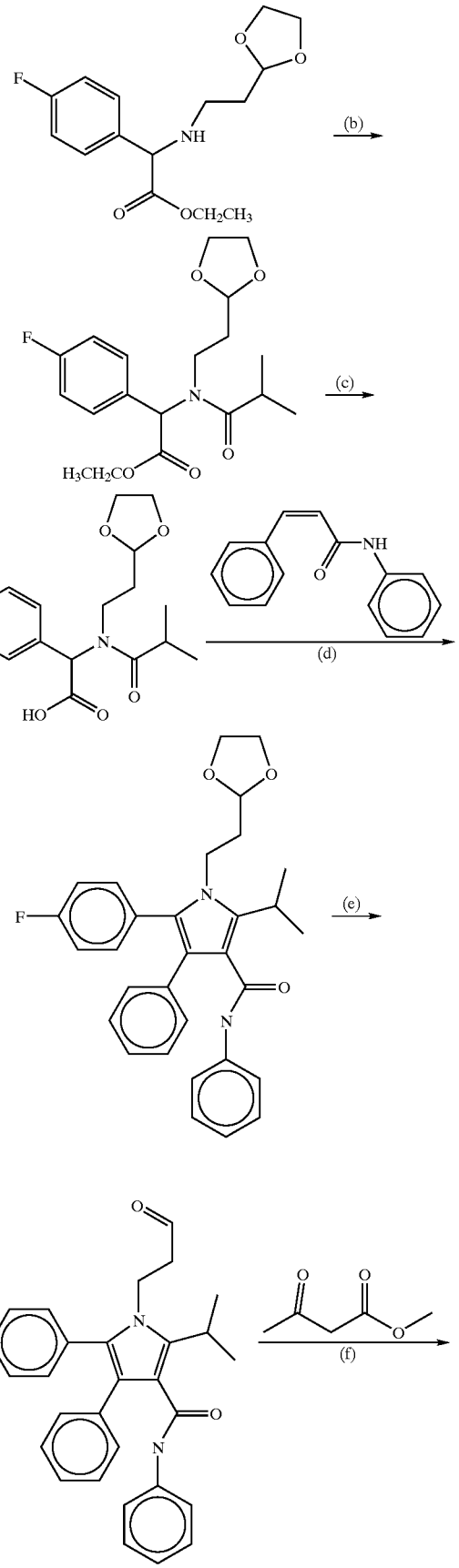

3
-continued

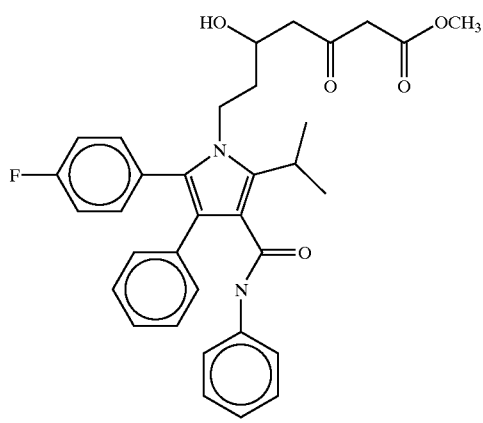

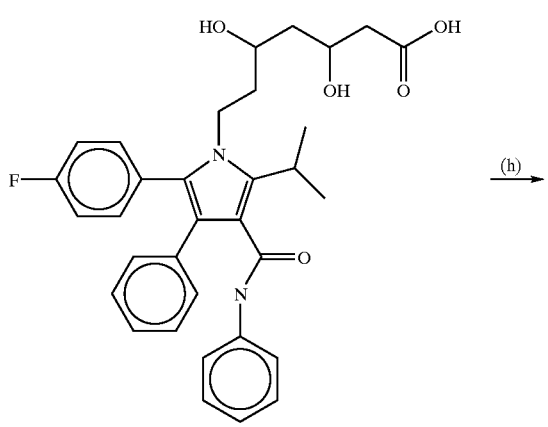

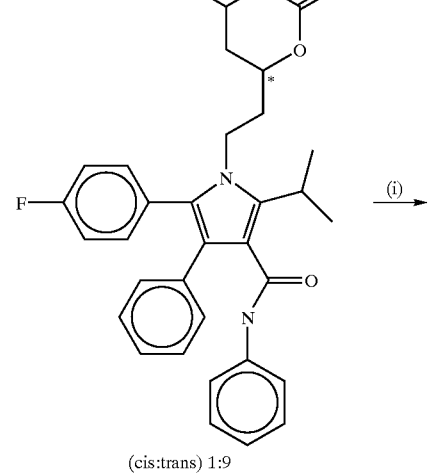

(cis:trans) 1:9

4
-continued

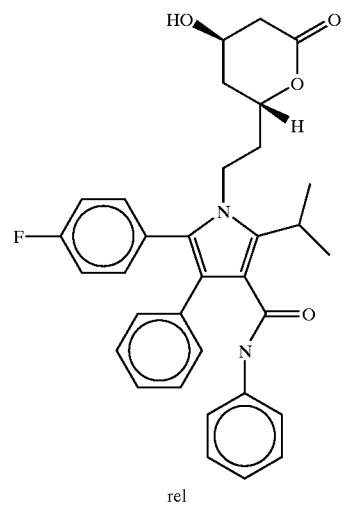

rel (a) Et₃N, CH₃CN; (b) isobutyryl chloride, Et₃N, CH₂Cl₂; (c) NaOH, MeOH:water; (d) 90° C.; (e) 1) HCl, EtOH, 2) PTSA, acetone:water; (f) 1) NaH, BuLi, THF; (g) 1) B(n-Bu)₃, THF, 2) NaBH₄; 3) aq. NaOH/H₂O₂; (h) Δ, tol. (i) recryst. tol./EA;

Example 2 of the '893 patent describes the preparation of the sodium salt of (R*,R*) -2-(4-fluorophenyl)-β,δ-dihydroxy-5-(1-methylethyl)-3-phenyl-4-[(phenylamino)carbonyl]-1H-pyrrole-1-heptanoic acid ("racemic atorvastatin sodium") by treating the racemic lactone with sodium hydroxide in THF:water, as shown in Scheme 2.

Scheme 2

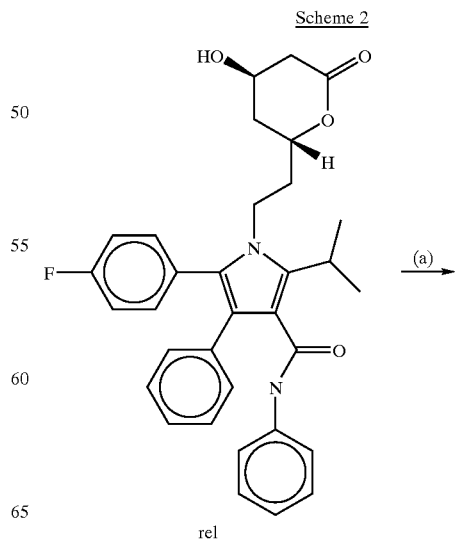

rel

5
-continued

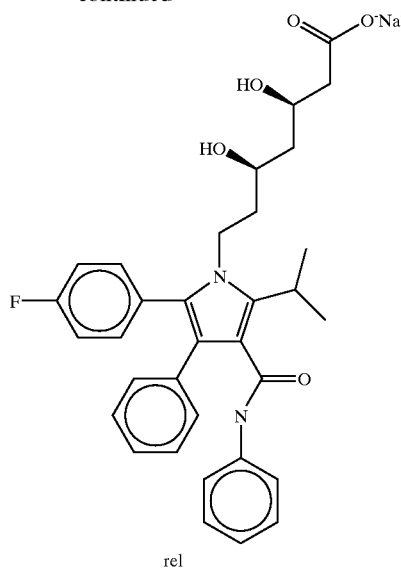

rel (a) NaOH, THF:water.

U.S. Pat. No. 5,273,995 discloses atorvastatin, the pure [R(R*,R*)] enantiomer of 2-(4-fluorophenyl)-β,δ-dihydroxy-5-(1-methylethyl)-3-phenyl-4-[(phenylamino) carbonyl]-1H-pyrrole-1-heptanoic acid. The '995 patent describes a stereoselective preparation (Scheme 3) of atorvastatin wherein the absolute configuration of the side chain hydroxy group closest to the pyrrole ring is set by a stereoselective aldol condensation. After chain extension with tert-butyl acetate, reduction of the β ketone proceeds under substrate stereocontrol to orient the β hydroxy group cis to the δ hydroxy group.

Scheme 3

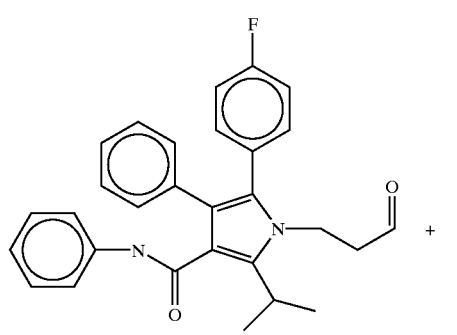

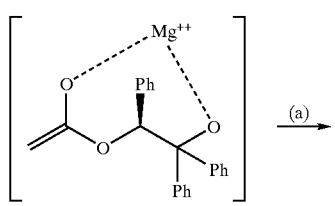

6
-continued

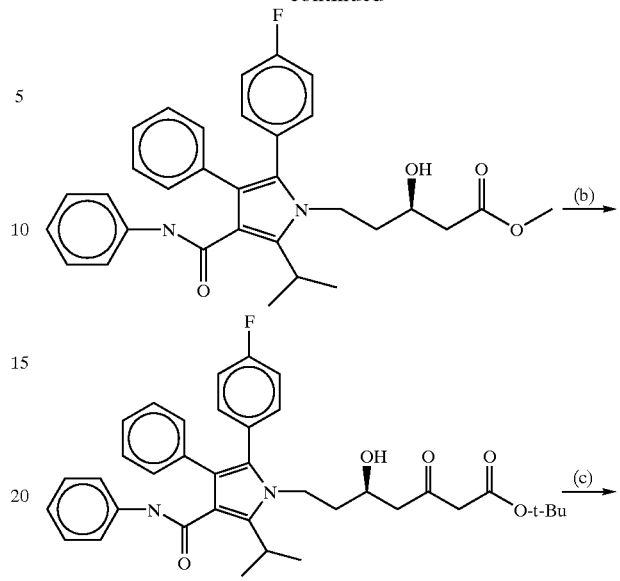

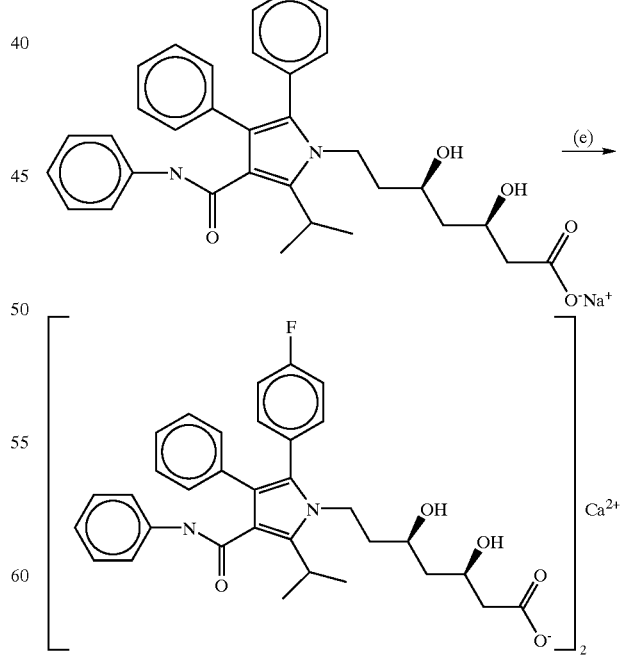

(a) 1) LDA, S-2-acetoxy-1,1,2-triphenylethanol, MgBr$_2$, THF, 2) $^+$Na$^-$OCH$_3$, MeOH:THF; (b) tert-butyl acetate, LDA, THF; (c) 1) BEt$_3$, NaBH$_4$, THF, 2) NaOH, THF:MeOH, 3) Δ, tol., 4) recryst. (d) 1 eq. NaOH (s), 5:1 MeOH:water; (e) 0.5 e q. CaCl$_2$·2H$_2$O.

The '995 patent describes a preparation of atorvastatin hemi-calcium, which is the salt form of the drug that has been approved by the U.S. Food and Drug Administration for oral administration to human patients. To prepare atorvastatin hemi-calcium, the '995 patent teaches that the sodium salt is prepared first by dissolving the lactone in methanol and water and adding a little less than one equivalent of sodium hydroxide to the solution until the lactone has been opened as determined by high performance liquid chromatography (HPLC). The '995 patent then teaches that the hemi-calcium salt may be prepared from the sodium salt by treating it with one equivalent or a slight excess of calcium chloride dihydrate ($CaCl_2.2H_2O$) (steps d and e of Scheme 3). To an atorvastatin sodium salt solution whose exact concentration has been determined by HPLC is slowly added an equivalent or slight excess of $CaCl_2.2H_2O$ at elevated temperature while agitating the solution. After completing the addition, atorvastatin hemi-calcium is obtained as a precipitate by cooling the solution. The '995 patent also describes how the pure R,R stereoisomer may be obtained from a mixture of R,R and S,S stereoisomers obtained from the '893 patent process.

U.S. Pat. No. 5,298,627 discloses an improved, more convergent, process for preparing atorvastatin in which the side chain bearing the β,δ-dihydroxy carboxylic acid—which is essential for biological activity—is incorporated in a single step (Scheme 4) rather than being elaborated from a propanal side chain as disclosed in the '893 and '995 patents.

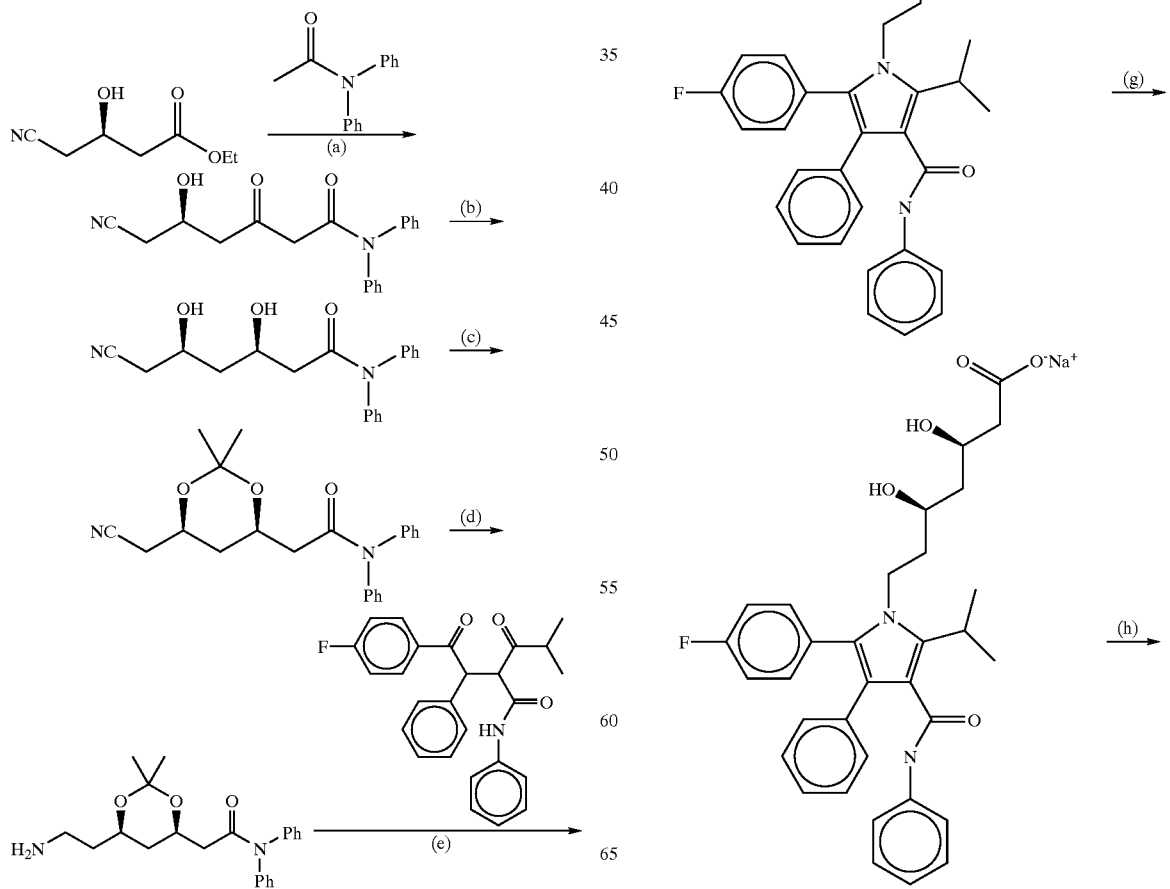

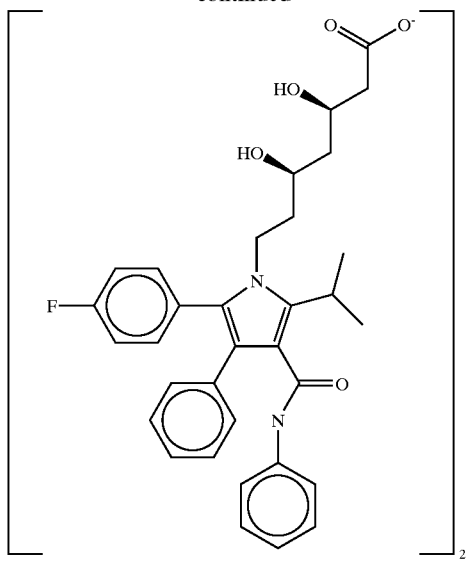

(a) LDA, THF; (b)B(OCH₃)Et₂, NaBH₄, 2:1 THF:CH₃OH; (c) 2,2-dimethoxypropane, MSA; (d) NH₃, Raney-Ni, MeOH; (e) pivalic acid, THF:tol.; (f) 1 N HCl, MeOH; (g) 2 N NaOH; (h) Ca(OAc)₂.

The convergent step of the process is a Paal Knorr reaction (step e). After the convergent step, the acetonide protecting group on the β and δ hydroxyls is cleaved with acid (step f). The '627 patent teaches that the sodium salt may be prepared from the N,N-diphenyl amide without intermediate isolation of the lactone by treating it with sodium hydroxide in a mixture of methanol and water (step g). The hemi-calcium salt is then prepared by dissolving the sodium salt in a solution of calcium acetate (Ca(OAc)₂) at room temperature and crystallizing the hemi-calcium salt from the solution by cooling. The '627 patent also describes preparations in which other N,N-disubstituted acetamides are used in the first step in otherwise similar processes. The '627 process is said to be well adapted for large scale production of atorvastatin.

Brower, P. L. et al. *Tet. Lett.* 1992, 33, 2279–82 states that (4R-cis)-1,1-dimethylethyl-6-cyanomethyl-2,2-dimethyl-1,3-dioxane-4-acetate is an ideal intermediate for preparing atorvastatin because it is highly crystalline and readily obtainable by recrystallization in high purity. After extensive optimization of the Paal-Knorr reaction, atorvastatin hemi-calcium was prepared from the highly crystalline intermediate in 60% yield following a procedure generally similar to steps (d) through (h) of Scheme 4. Baumann, K. L. et al. *Tet. Lett.* 1992, 33, 2283–2284. Conversion of the Paal Knorr reaction product to atorvastatin hemi-calcium was carried out without isolation of intermediate products by deprotection of the acetonide with aqueous HCl/methanol, dilute base hydrolysis of the tert-butyl ester (anchimeric assistance) and treatment of the derived sodium salt with Ca(OAc)₂ as shown in Scheme 5. As in the process of the '627 patent previously described, the carboxyl protecting group was cleaved with sodium hydroxide and atorvastatin hemi-calcium was prepared by treating the sodium salt with calcium acetate.

Scheme 5

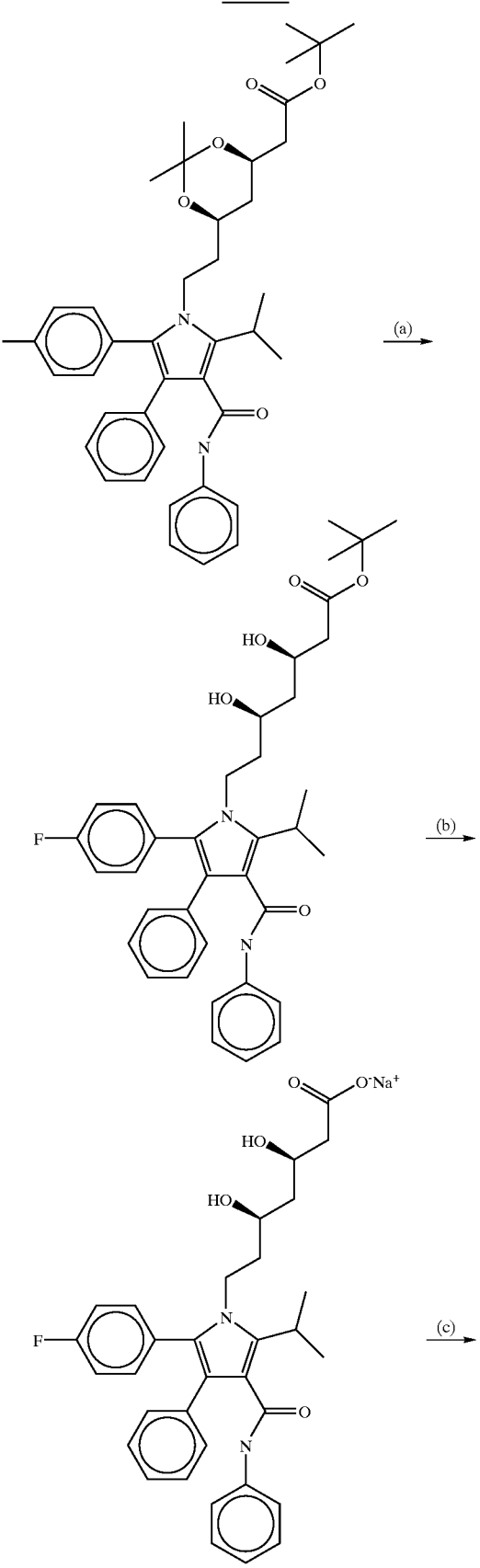

-continued

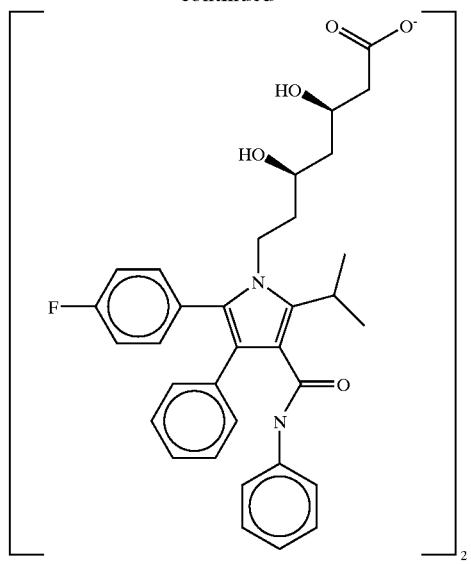

(a) HCl, MeOH; (b) NaOH; (c) Ca(OAc)$_2$

U.S. Pat. Nos. 5,003,080; 5,097,045; 5,124,482; 5,149,837; 5,216,174; 5,245,047 and 5,280,126 disclose methods of making atorvastatin free acid and lactone and/or stereoisomers thereof. Roth, B. D. et al. *J. Med. Chem.* 1991, 34, 357–66 discloses preparations of atorvastatin lactone and other pyrrol-1-yl ethylmevalonolactones with variable substituents on the pyrrole ring.

Kearney, A. S. et al. "The Interconversion Kinetics, Equilibrium, and Solubilities of the Lactone and Hydroxyacid Forms of the HMG-CoA Reductase Inhibitor, CI-981" *Pharm. Res.* 1993, 10, 1461–65 reports that the carboxylic acid group of atorvastatin has a $PK_a$ of 4.46. The acidic proton of the carboxylic acid group of intermediate compounds used to prepare atorvastatin by the '893 and '995 patent processes must be masked during the chain elaboration steps. The carboxyl group is also protected during the Paal Knorr reaction in the '627 patent and Baumann et al. processes. Forming an ester is a well known way of protecting a carboxylic acid group and masking its acidic proton. Green, T. W.; Wuts, P. G. M. *Protective Groups in Organic Synthesis* 3rd. ed., chapter 5 (John Wiley & Sons: New York 1999) ("Greene & Wuts"). It is also known, generally, that carboxylic acids that have been protected as esters may be deprotected by hydrolyzing the ester with a strong base. Id. at 377–78.

Sodium hydroxide is a strong base with a dissociation constant of 6.37 ($pK_b=-0.80$), *Handbook of Chemistry and Physics* 81st ed. 8–45 (CRC Press: Boca Raton 2000–01), and its use as a reagent for deprotecting ester-protected carboxylic acids is taught in the art. Green & Wuts, p. 377. Calcium hydroxide (Ca(OH)$_2$), with a first dissociation constant of $3.74\times10^{-3}$ ($pK_b=2.43$) and second dissociation constant of $4.0\times10^{-2}$ ($pK_b=1.40$), is a much weaker base than sodium hydroxide. *Handbook of Chemistry and Physics* 63rd ed. D-170 (CRC Press: Boca Raton 1983).

Calcium hydroxide is not listed among the reagents that have been used to hydrolyze esters in a well known compendium of functional group transformations in organic synthesis. Larock R. C. *Comprehensive Organic Transformations* 2nd ed, Section Nitriles, Carboxylic Acids and Derivatives, Sub-sect. 9.17, pp. 1959–68 (Wiley-VCH: New York 1999). Its use as a general reagent for deprotecting ester-protected carboxylic acids is not taught by a well known reference book on methods for protecting and deprotecting organic functional groups. Greene & Wuts. pp. 377–79. In fact, the '995 patent cautions against using an excess of sodium hydroxide to prepare the sodium salt in order to prevent forming calcium hydroxide when calcium chloride is later added to a solution of the sodium salt. It appears not to have been appreciated that an ester-protected form of atorvastatin can be converted directly to atorvastatin hemi-calcium without first treating the ester with a strong base like sodium hydroxide to hydrolyze it.

The present invention meets a long-felt need for a more direct, practicable, convenient and high yielding route to atorvastatin hemi-calcium from a carboxylic acid ester derivative of atorvastatin.

SUMMARY OF THE INVENTION

It has now been discovered that an atorvastatin carboxylic acid ester derivative can be converted directly to atorvastatin hemi-calcium with calcium hydroxide. The calcium hydroxide performs two functions. It is a basic catalyst for hydrolyzing the carboxylic acid ester and it supplies calcium ion to coordinate with atorvastatin carboxylate anions to form atorvastatin hemi-calcium.

Accordingly, the present invention provides a process for preparing atorvastatin hemi-calcium by converting an atorvastatin ester derivative of formula:

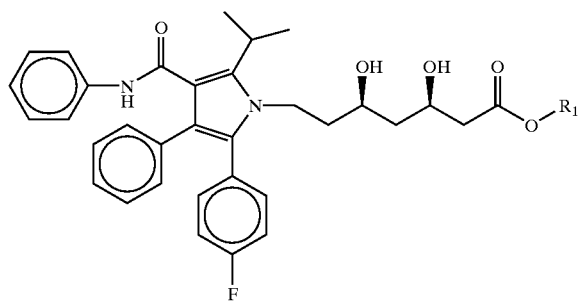

wherein $R_1$ is a lower alkyl group, to atorvastatin hemi-calcium with calcium hydroxide.

The process is advantageously practiced in a process provided by this invention for converting a dioxanyl derivative of atorvastatin of formula:

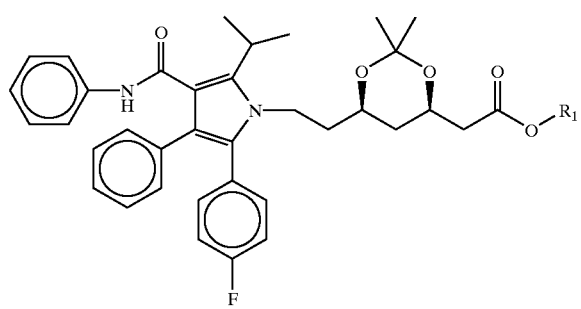

wherein $R_1$ is as previously defined, to atorvastatin hemi-calcium, hereafter referred to as the sequential acid-base hydrolysis process. The sequential acid-base hydrolysis process may be conveniently practiced by following one of the exemplary embodiments.

In one exemplary embodiment, the sequential acid-base hydrolysis process is performed in two steps with intermediate isolation of an atorvastatin ester derivative. The isolated atorvastatin ester derivative may be the direct product of hydrolysis of the dioxane and have the structural formula 1. Another atorvastatin ester derivative resulting from ester transposition with an alcohol solvent and/or atorvastatin lactone may also be obtained, optionally in mixture with some atorvastatin free acid. First, the dioxane 2 is converted to one or more of these atorvastatin ester derivatives with an acid catalyst, preferably acetic acid. The atorvastatin ester derivative or mixture thereof is then isolated in condensed form, i.e. as a solid or oil. Second, the isolated atorvastatin ester derivative(s) is converted to atorvastatin hemi-calcium with calcium hydroxide and, optionally, a phase transfer agent.

In another exemplary embodiment, dioxane 2 is hydrolyzed in a mixture of an acid catalyst and a mixed solvent comprising a $C_1$–$C_4$ alcohol of formula $R_2$—OH and water to form the atorvastatin ester derivative 1 or another atorvastatin ester derivative, optionally in mixture with some atorvastatin free acid. The ester derivative(s) is then converted to atorvastatin hemi-calcium with calcium hydroxide in a solution of a $C_1$–$C_4$ alcohol. The steps of the second embodiment of the sequential acid-base hydrolysis process are advantageously practiced in a single reaction vessel, i.e. as a "one-pot" process. In either embodiment of the acid-base process, atorvastatin hemi-calcium, or a solvate thereof, may be separated from the solvent and dissolved substances by precipitation.

DETAILED DESCRIPTION OF THE PREFERRED EMBODIMENTS

Some of the terms used in this disclosure have the following ascribed meanings.

A $C_1$–$C_4$ alcohol is a compound of the formula $R_2$—OH wherein $R_2$ is methyl, ethyl, propyl, isopropyl, n-butyl, s-butyl or t-butyl.

An "ester derivative" is a compound resulting from replacement of the hydroxyl proton of a carboxylic acid with a substituent bonded to the hydroxyl oxygen atom through carbon. Unless otherwise excluded by a formula, an ester derivative includes a lactone, which is a cyclic ester in which the ester group in incorporated into a ring. Ester derivatives also include compounds where the substituent bonded to the hydroxyl oxygen is $C_1$–$C_4$ alkyl group.

In its first aspect, the present invention provides a process for preparing atorvastatin hemi-calcium by converting an atorvastatin ester derivative of formula:

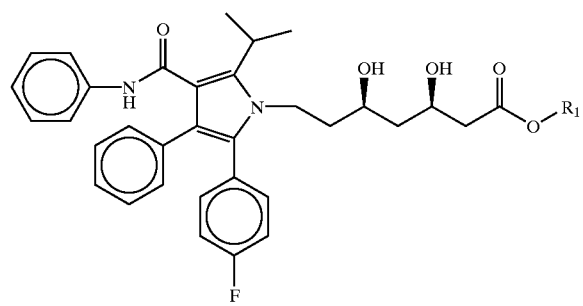

1 wherein $R_1$ is a $C_1$ to $C_4$ alkyl, to atorvastatin hemi-calcium with calcium hydroxide. An unexpected advantage of this process is that the calcium hydroxide fulfills two roles. It functions as a basic catalyst for hydrolysis of the ester and supplies calcium ion that coordinates to atorvastatin anions. Another significant practical advantage of the process is that the amount of calcium hydroxide does not have to be as carefully controlled as the amount of sodium hydroxide and calcium chloride used in other processes.

The atorvastatin ester derivative 1 may be provided in pure form or in mixture with other atorvastatin ester derivatives. In a second aspect of the invention, described below, a mixture of intermediate atorvastatin ester derivatives are formed from a dioxanyl precursor compound. These atorvastatin ester derivatives include, in addition to those of formula 1, those derived from transposition of atorvastatin ester derivative 1 with a $C_1$–$C_4$ alcohol solvent of formula $R_2$—OH. In addition, atorvastatin ester derivative 1 may be provided in mixture with atorvastatin lactone, which may form from atorvastatin free acid, small amounts of which are in equilibrium with the ester in the acidic aqueous solvents used in the second aspect of this invention.

In the invention's first aspect, hereafter referred to as the base hydrolysis process, the atorvastatin ester derivative 1, optionally in mixture with other atorvastatin ester derivatives, is dissolved or suspended in a mixed solvent comprising a $C_1$–$C_4$ alcohol and water. A preferred alcohol is ethanol and a preferred solvent mixture contains about 5% to about 15% water in ethanol, more preferably about 10% water and about 90% ethanol (v/v). Whether the atorvastatin ester derivative 1 dissolves in the mixed solvent depends upon such factors as the choice of $C_1$–$C_4$ alcohol, the proportion of water, the temperature and the purity of the atorvastatin ester derivative. Calcium hydroxide is suspended in the mixed solvent and the base hydrolysis reaction mixture is maintained until the atorvastatin ester derivative 1 has been consumed. Consumption of atorvastatin ester derivative 1 may be monitored by any conventional means like TLC, HPLC, NMR and the like. After the atorvastatin ester derivative 1 has been consumed, atorvastatin hemi-calcium is recovered from the base hydrolysis reaction mixture by any means. It is unnecessary to add another source of calcium to provide a $Ca^{2+}$ ion for the atorvastatin hemi-calcium salt.

According to a preferred procedure for practicing the base hydrolysis process, the atorvastatin ester derivative 1 is added in an amount sufficient to provide about 10 mmoles $L^{-1}$ to about 1 mole $L^{-1}$ of the mixed solvent.

Preferably, about 1 equivalent to about 6 equivalents of calcium hydroxide with respect to the ester derivative 1 is used. More preferably, from about 1 to about 2 equivalents is used.

Calcium hydroxide is only sparingly soluble in the $C_1$–$C_4$ alcohol:water mixed solvent and only a minor proportion of it will be in solution available to catalyze the hydrolysis at any one time. To accelerate the base hydrolysis, a phase transfer catalyst may be added to increase the solubility of the calcium hydroxide. Phase transfer catalysts are well known in the art and include, for instance, tetra-n-butylammonium bromide ("TBAB"), benzyltriethylammonium chloride ("TEBA"), tetra-n-butylammonium chloride, tetra-n-butylammonium bromide, tetra-n-butylammonium iodide, tetra-ethylammonium chloride, benzyltributylammonium chloride, benzyltributylammonium bromide, benzyltriethylammonium bromide, tetramethylammonium chloride and polyethylene glycol. A most preferred phase transfer catalyst is TBAB. When used, the phase transfer catalyst should be used in a substoichiometric amount, preferably from about 0.05 to about 0.25 equivalents, more preferably about 0.1 equivalents, with respect to atorvastatin ester derivative 1.

The mixture may be heated to up to the reflux temperature of the mixed solvent in order to accelerate the reaction. A preferred temperature range is from about 30° C. to about 70° C.

After consumption of atorvastatin ester derivative 1, atorvastatin hemi-calcium or solvate thereof is recovered from the base hydrolysis reaction mixture. As part of recovering the atorvastatin hemi-calcium, the reaction mixture should be filtered to remove excess suspended calcium hydroxide. The reaction mixture preferably is filtered hot to prevent precipitation of atorvastatin hemi-calcium on the calcium hydroxide filtercake.

After filtration to remove suspended calcium hydroxide, atorvastatin hemi-calcium may be recovered from the filtrate by precipitation. According to a preferred recovery technique, atorvastatin hemi-calcium is caused to precipitate from the filtrate by slow addition of water. A volume of water roughly equivalent to the volume of the filtrate is added over about an hour's time. Preferably, the slow water addition is also conducted at elevated temperature, e.g from about 40° C. to about 65° C. Precipitating atorvastatin hemi-calcium by slow water addition yields atorvastatin hemi-calcium in a crystalline trihydrate state and prevents formation of a gelatinous precipitate. Alternatively, atorvastatin hemi-calcium may be recovered by any conventional means. After any necessary purification steps, the recovered atorvastatin hemi-calcium may be used as an active ingredient to formulate a pharmaceutical product.

In a second aspect of the invention, the base hydrolysis process for converting atorvastatin ester derivative 1 to atorvastatin hemi-calcium is preceded by acid hydrolysis of a dioxane of formula:

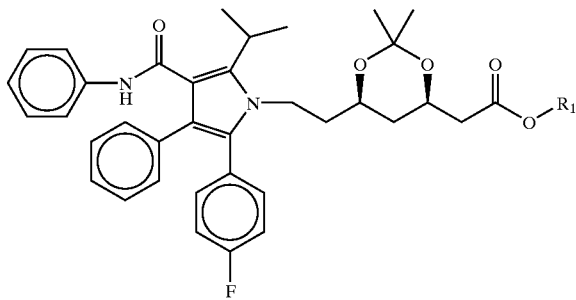

2 wherein $R_1$ is as previously defined. This two-step process (which may be conducted in single reaction vessel) is hereafter referred to as the sequential acid-base hydrolysis process.

Dioxane 2 is an important intermediate in the preparation of atorvastatin. For example, it is an intermediate in the Baumann et al. process. Dioxane 2 is a protected form of atorvastatin with an acetonide protecting group on the β,δ-dihydroxy groups and an ester group masking the carboxylic acid proton.

According to one preferred embodiment of the sequential acid-base hydrolysis process, dioxane 2 is converted into an atorvastatin ester derivative or mixture thereof, which is then isolated as a solid or oil before being carried forward to prepare atorvastatin hemi-calcium according to the base hydrolysis process of the invention. In this embodiment, the dioxane ring of dioxane 2 is cleaved with a catalyst selected from the group consisting of acetic acid, trifluoroacetic acid, p-toluenesulfonic acid, zinc bromide and hydrochloric acid. Procedures for practicing this process using these catalysts are illustrated in Example 1. In its most preferred mode, this embodiment uses acetic acid as an 80% solution in water (Example 1 (a)–(c)). Dioxane 2 is suspended in the aqueous acetic acid and stirred at room temperature until a clear solution is obtained. The acetic acid is then evaporated under reduced pressure. Remaining traces of acetic acid may be removed by azeotroping with toluene, leaving a residue of atorvastatin ester derivative 1 as a solid or as a viscous oil containing residual toluene. The residue may also contain amounts of atorvastatin lactone and atorvastatin free acid.

As further illustrated in Example 2, the residue may be converted to atorvastatin hemi-calcium by suspending in the $C_1$–$C_4$ alcohol:water mixed solvent and adding from about 1 to about 6, more preferably in this embodiment from about 4 to about 6 equivalents of calcium hydroxide and a phase transfer agent. After the atorvastatin ester derivative 1 has been consumed, the mixture is filtered to remove excess calcium hydroxide. Atorvastatin hemi-calcium or solvate thereof may then be recovered by precipitation, e.g., by cooling the solution and/or adding water (for example as previously described for the base hydrolysis process), filtering and drying. The filtrate also may be further purified by recrystallization using known techniques or by chromatography.

In another preferred embodiment of the sequential acid-base hydrolysis process, both the acid hydrolysis of the 1,3-dioxane ring of dioxane 2 and the subsequent base hydrolysis of the ester are performed in a mixed solvent of a $C_1$–$C_4$ alcohol and water. Thus, this embodiment of the sequential acid-base hydrolysis process may be advantageously practiced entirely in one reaction vessel without a change of solvent or isolation of an atorvastatin ester intermediate or mixture of intermediates. An additional advantage of this "one-pot" embodiment is that it enables further reduction of the amount of calcium hydroxide used, yet without demanding strict adherence to a predetermined exact molar ratio. The one-pot embodiment also does not involve using a phase transfer agent and uses a mineral acid to cleave the 1,3 dioxane ring, thus reducing the cost of reagents.

In the one-pot embodiment of the sequential acid-base hydrolysis process, dioxane 2 is suspended in the mixed alcohol:water solvent in a vessel that is able to withstanding a vacuum and is equipped with a heater and a distillation head. The mixed solvent is pH adjusted to about 1 or less with hydrochloric acid or other mineral acid. Hydrochloric acid is preferred because a small amount of calcium chloride is formed when calcium hydroxide is added to the reaction mixture. Calcium chloride is readily soluble in the mixed solvent and therefore easily separated from the product when atorvastatin hemi-calcium is precipitated from the reaction mixture. The mixed solvent is conveniently prepared and pH adjusted by mixing dilute aqueous hydrochloric acid with the $C_1$–$C_4$ alcohol, from 1.5% to 10% hydrochloric acid being preferred.

Dioxane 2 is preferably added in an amount of about 0.12 moles $L^{-1}$ of the $C_1$–$C_4$ alcohol. The resulting suspension may be heated to accelerate hydrolysis of the dioxane. Preferred temperatures for the hydrolysis are mildly elevated, ranging from about 30° C. to about 50° C., more preferably about 40° C.

Under acidic aqueous conditions, the dioxane 2 and free diol 1 are in equilibrium. Under the preferred reaction conditions, the mixed solvent contains something on the order of a ten fold molar excess of water over the amount of acetone that would be produced by complete hydrolysis. A significant amount of the dioxane would remain in the reaction mixture if acetone were not removed. Therefore, it is desirable to remove acetone that is liberated by the acid hydrolysis from the reaction vessel by evaporation To meet this purpose at the preferred reaction temperatures, the reaction vessel should be maintained under sufficiently reduced pressure to distill off the liberated acetone. Aspirator vacuum is generally sufficient. Alcohol and water vapors may be drawn off by the distillation head along with the acetone. Make up alcohol may be added to the mixture to maintain a constant volume. Consumption of dioxane 2 may be monitored by HPLC chromatography, or by observing the formation of a clear solution and allowing a period of about 9 to 11 hrs for consumption of dissolved dioxane 2.

Acid hydrolysis of dioxane 2 produces atorvastatin ester derivative 1 as a direct product. However, other reactions occur to a greater or lesser extent under these conditions. Transesterification occurs with the alcohol solvent component to form atorvastatin ester derivatives of formula:

3

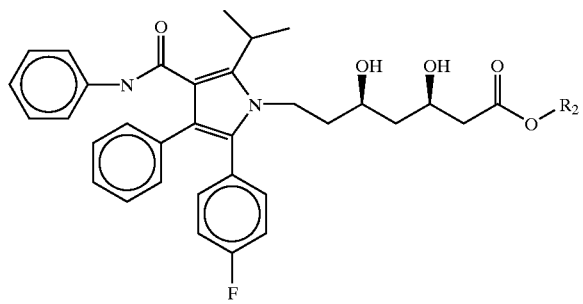

wherein $R_2$ is the alkyl substituent of the $C_1$-$C_4$ alcohol, and may be the same or different from $R_1$. In the presence of water, some atorvastatin free acid forms. The free acid in turn lactonizes, although a proportion remains in equilibrium as the free acid with the lactone and with the other atorvastatin ester derivatives.

After dioxane 2 has been completely consumed, calcium hydroxide is added to the resulting solution. The rate of hydrolysis of the atorvastatin ester derivatives by calcium hydroxide depends upon a variety of factors including the temperature, concentration of the ester derivatives in the mixture, the exact composition of the mixture, all of which can vary in accordance with the invention. The rate of hydrolysis also depends upon the quantity and particle size of the calcium hydroxide used. With these considerations in mind, an optimal set of base hydrolysis conditions using calcium hydroxide has been developed.

The total atorvastatin ester derivative concentration, which is taken as equal to the concentration of dioxane 2, is adjusted to from about 0.10 to about 0.15 M, by continuing to distill solvent or by adding more $C_1$-$C_4$ alcohol and/or water. Any amount of calcium hydroxide in excess of about ¾ molar equivalent with respect to the dioxane 2 may be used. However, in the one-pot embodiment of the sequential acid-base hydrolysis process, preferably from about 1 to about 2 equivalents, more preferably about 1.5 molar equivalents of calcium hydroxide with respect to the atorvastatin ester derivatives (or dioxane 2) is used. Calcium hydroxide may be added in one or more than one portion. Further, the reaction mixture is preferably heated to from about 50° C. to about 70° C., more preferably about 70° C. Under these conditions, the atorvastatin ester derivative(s), i.e. compound 1, transposed ester 3, and atorvastatin lactone are substantially completely hydrolyzed within a few hours. The consumption of the atorvastatin ester derivatives may be monitored by HPLC. Using these conditions, atorvastatin hemi-calcium can be later precipitated from the base hydrolysis reaction mixture substantially free of impurities, i.e. containing less than 0.05%, atorvastatin ester derivative 1.

After the atorvastatin ester derivatives have been consumed, excess suspended calcium hydroxide should be filtered from the mixture if it is desired to precipitate atorvastatin hemi-calcium from the base hydrolysis reaction mixture with minimal contamination by calcium hydroxide. The reaction mixture preferably is filtered hot to prevent precipitation of atorvastatin hemi-calcium on the calcium hydroxide filtercake. Using the preferred amount of 1 to 2 equivalents of calcium hydroxide in the one-pot process also minimizes losses due to precipitation of atorvastatin hemi-calcium on the calcium hydroxide filter cake and increases the purity of the atorvastatin hemi-calcium recovered from the solution by precipitation.

Further, according to the preferred mode of practicing the one-pot sequential acid-base hydrolysis process, atorvastatin hemi-calcium is caused to precipitate from the filtrate by slow addition of water as previously described with reference to the base hydrolysis process. The precipitate may be carried forward and used in a pharmaceutical product.

The filtering characteristics and purity of the atorvastatin hemi-calcium may be further improved by redissolving the crystalline product in the aqueous alcohol reaction mixture by heating to a temperature sufficient to cause all the precipitate to dissolve, resulting in a clear solution. The solution should then be slowly cooled over several hours and held, preferably at ambient temperature, until no more crystals are observed to form. After filtering and drying, and any necessary purification steps, the atorvastatin hemi-calcium or solvate thereof may be used as an active ingredient in a pharmaceutical product.

Having thus described the present invention with reference to certain of its preferred embodiments, it will now be further illustrated with the following examples which offer highly specific procedures that may be followed in practicing the invention but which should not be construed as limiting the invention in any way.

EXAMPLES

General

Unless otherwise indicated, reagents were used as received. [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (dioxane 2,$R_1$=t-Butyl) was prepared by a condensation reaction between the corresponding diketone and the corresponding chiral amine to form the pyrrole ring. It also may be prepared by known methods. Brower, P. L. et al. Tet. Lett. 1992, 33, 2279–82; Baumann, K. L. et al. Tet. Lett. 1992, 33, 2283–84. The following HPLC conditions were used to determine the composition of mixtures obtained in the acid hydrolyses reported in the examples: Waters Spherisorb S3 ODS1 (7.6×100 mm), 70:30 acetonitrile:water, 0.6 ml min.$^{-1}$, 20 μl sample, UV detection λ=254).

Example 1

Preparation of Atorvastatin Ester Derivative(s) From Dioxane 2 a) Dioxane 2 ($R_1$=t-Bu) (2.0 g, 3.06 mmole) was suspended in an 80% aqueous solution of acetic acid (50 ml) in a flask equipped with a magnetic stirrer. The mixture was stirred at ambient temperature for 20 hours until a clear solution was obtained. The clear solution was evaporated to dryness and traces of acetic acid were removed by azeotropic distillation with toluene (3×50 ml) to obtain a powder containing atorvastatin t-butyl ester 1 ($R_1$=t-Bu), atorvastatin free acid and atorvastatin lactone.

b) Dioxane 2 ($R_1$=t-Bu) (10.0 g, 15.3 mmole) was suspended in an 80% aqueous solution of acetic acid (150 ml) in a flask equipped with a magnetic stirrer. The mixture was stirred at ambient temperature overnight until a clear solution was obtained. The clear solution was evaporated and the traces of acetic acid were removed by azeotropic distillation with toluene (3×100 ml) to obtain an oil containing toluene, atorvastatin t-butyl ester 1 ($R_1$=t-Bu), atorvastatin free acid and atorvastatin lactone.

c) In a flask equipped with a magnetic stirrer, dioxane 2 ($R_1$=t-Bu) (1.0 g, 1.53 mmol) was suspended in 80% aqueous acetic acid (10 ml) containing p-toluenesulfonic acid (40 mg, 0.21 mmole). The mixture was stirred at ambient temperature for 18 hours. The white precipitate that appeared was filtered, wash with water (3×15 ml), and dried in a vacuum oven at 50° C. for about 4 hours to yield a powder containing atorvastatin t-butyl ester 1 ($R_1$=t-Bu), atorvastatin free acid and atorvastatin lactone.

d) To a flask equipped with a magnetic stirrer, dioxane 2 ($R_1$=t-Bu) (0.5 g, 0.76 mmole) was dissolved in a 1:1 mixture of trifluoroacetic acid:tetrahydrofuran (4 ml ) in the presence of catalytic amount of water. The reaction mixture was stirred at ambient temperature for 24 hours. The solution obtained was evaporated and traces of trifluoroacetic acid were removed by azeotropic distillation with ether (3×10 ml) leaving a white solid residue (0.3 g). Based on HPLC analysis, the white solid was a mixture of atorvastatin free acid and atorvastatin lactone in the ratio of 40:60.

e) A flask equipped with a magnetic stirrer was charged with dichloromethane (5 ml), dioxane 2 ($R_1$=t-Bu) (0.2 g, 0.30 mmole) and zinc bromide (241 g, 1.07 mmole, 3.5 eq). The reaction mixture was stirred at ambient temperature for 24 h. Water (30 ml) was added and the mixture was stirred for an additional 3 hours. The aqueous layer was extracted with dichloromethane (3×10 ml) and the organic layer was dried with sodium sulfate and filtered. The organic layer was then evaporated under reduced pressure to give a powder (150 mg). Based on HPLC analysis, the powder was a mixture of atorvastatin free acid and atorvastatin lactone in the ratio of 57:43.

f) In a flask equipped with a magnetic stirrer, dioxane 2 ($R_1$=t-Bu) (0.2 g, 0.31 mmole) was suspended in a 90% aqueous solution of acetic acid (4 ml). The mixture was stirred at 60° C. for 5 days. The resulting solution was evaporated to dryness and traces of acetic acid were removed by azeotropic distillation with toluene (3×15 ml) leaving a powder residue. Based on HPLC analysis, the powder was a mixture of atorvastatin free acid and atorvastatin lactone in the ratio of 54:46.

g) In a flask equipped with a magnetic stirrer, dioxane 2 ($R_1$=t-Bu) (0.2 g, 0.31 mmole) was dissolved in a mixture of 3% aqueous solution of hydrochloric acid (1 ml) and methanol (2 ml). The mixture was stirred at 100° C. for 3.5 hours and then stirred overnight at ambient temperature. The resulting solution was evaporated to dryness to obtain a powder. Based on HPLC analysis, the powder was a mixture of atorvastatin free acid and atorvastatin lactone in the ratio 54:46.

Example 2

Preparation of Atorvastatin Hemi-calcium from the Ester Derivative(s)

a) A saturated solution of calcium hydroxide (8 ml) containing tetrabutyl ammonium bromide (10 mg, 0.031 mmole) was added to a solution of the powder obtained in Example 1(a) (200 mg, 0.32 mmole) in ethanol (8 ml). The mixture was stirred and heated to 45° C. for 24 hours. Additional saturated calcium hydroxide solution (4 ml) was then added. After 20 more minutes of stirring at ambient temperature, HPLC of the reaction mixture showed that the reaction was complete. A white precipitate from the reaction mixture was filtered under vacuum and dried at 65° C. for about 18 hours to give atorvastatin hemi-calcium (142 mg, 77%).

b) The oil obtained from Example 1(b) was dissolved in a mixture of ethyl alcohol (100 ml) and water (20 ml). Calcium hydroxide (6.22 g, 84.0 mmole, 5.5 eq.) and tetrabutyl ammonium bromide (0.46 g, 1.43 mmole, 0.05 eq.) were added. The mixture was heated to 45° C. for 3 hours until the reaction was complete. While the mixture was still hot, it was filtered under vacuum to remove excess calcium hydroxide. The mixture was then cooled to ambient temperature, after which, while stirring, water (200 ml) was added. A white precipitate that formed was filtered under vacuum and dried at a temperature of about 65° C. for about 18 hours to give atorvastatin hemi-calcium (7.44 g, 84%).

Example 3

Preparation of Atorvastatin Hemi-calcium from Dioxane 2 in One-Pot a) Dioxane 2 ($R_1$=t-Bu) (20 g, 30.6 mmole) was suspended in a mixture of 1.5% HCl (50 ml, 0.067 eq. HCl, 11.2 eq. water) and absolute ethanol (250 ml) in a cylindrical reactor equipped with a distillation apparatus and a mechanical stirrer. The suspension was heated to 40° C. and then the pressure inside the reactor was reduced to 500–600 mbar for 9–11 hrs while a vapor mixture of acetone, ethanol and water was continuously distilled off. Make-up of absolute Ethanol (35–40 ml.) was added every hour. After 9–11 hours, dioxane 2 ($R_1$=t-Bu) had been more than 99.9% consumed according to HPLC and the suspension had become a clear solution.

Without any further treatment, $Ca(OH)_2$ (3.4 g, 46 mmole, 1.5 eq.) was added. The reaction mixture was heated to 70° C. for 4–5 hrs. Then, the excess of $Ca(OH)_2$ was collected by filtration. To the hot filtrate (65° C.), water (350 ml) was added slowly using a dosing pump over about ¾ of an hour to 1 hour. During the addition, atorvastatin hemi-calcium precipitated. The atorvastatin hemi-calcium can be filtered at this point, but that was not done in order to obtain a product with optimal filtering characteristics and a low level of impurities.

After the addition of water was complete, the reaction mixture was heated to reflux (84° C.) until the mixture clarified. The mixture was then cooled to 20° C. over 3 hrs and stirred at this temperature for an additional 20 hrs. The solid was then filtered to give 45.0 g of wet cake of Atorvastatin hemi-calcium. The wet cake was dried at 65° C. for 24 hrs to give atorvastatin hemi-calcium (16.7 g, 95%) with a water content of between 2.8% and 6.6% as determined by Karl-Fisher analysis.

b) Dioxane 2 ($R_1$=t-Bu) (20 g, 30.6 mmole) was suspended in a mixture of 10% HCl (7.6 ml, 0.68 eq. HCl, 12.4 eq. water) and methanol (135 ml) in a cylindrical reactor equipped with a distillation apparatus and a mechanical stirrer. The suspension was heat to 35° C. for 3 hrs, while the pressure inside the reactor was reduced to 820 mbar and a vapor mixture of acetone, methanol and water was continuously distilled off. Make-up of methanol (35 ml)

was added every ½ hour. After 3 hrs dioxane 2 ($R_1$=t-Bu) had been more than 99.9% consumed according to HPLC and and the suspension had become a clear solution.

Without any further treatment, $Ca(OH)_2$ (3.4 g, 45.9 mmole, 1.5 eq), water (5 ml) and methanol (45 ml) were added. The reaction mixture was heated to 70° C. for 2 hrs. The excess of $Ca(OH)_2$ was collected by filtration and the $Ca(OH)_2$ cake was washed with methanol (2×10 ml). To the hot filtrate (65° C.), water (300 ml) was slowly added using a dosing pump over 45 minutes. During the addition, atorvastatin hemi-calcium salt precipitated. The atorvastatin hemi-calcium can be filtered at this point, but that was not done in order to obtain a product with optimal filtering characteristics and a low level of impurities.

After the addition, the reaction mixture was heated to reflux temperature (78° C.) for ½ hour. The mixture was then cooled to 20° C. over 3 hrs and stirred at this temperature for another 20 hrs. The solid was then filtered and dried at 65° C. for 48 hrs to give atorvastatin hemi-calcium (16.9 g, 96%) with a water content of 3.2% by Karl Fisher analysis.

Having thus described the invention with reference to certain illustrative embodiments and further illustrated it with examples, those skilled in the art may, upon reading the description and examples, appreciate variations that could be made which do not depart from the spirit and scope of the invention as defined by the claims which follow.

We claim:

1. A process for preparing atorvastatin hemi-calcium comprising:
   a) providing an atorvastatin ester derivative of formula:

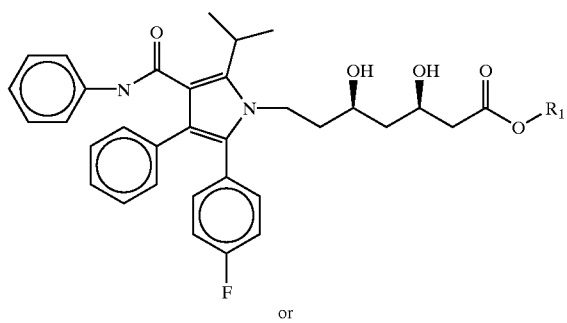

or

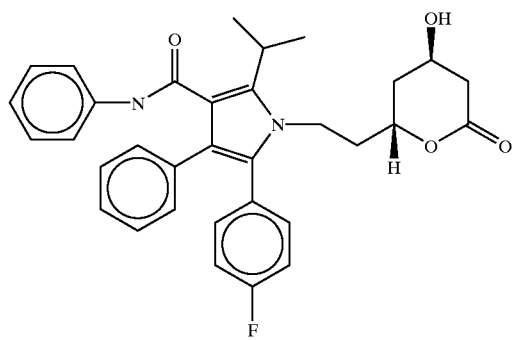

wherein $R_1$ is a $C_1$–$C_4$ alkyl group, and
   b) converting the atorvastatin ester derivative to atorvastatin hemi-calcium with calcium hydroxide.

2. The process of claim 1 wherein the atorvastatin ester derivative is provided in a mixture with a second atorvastatin ester derivative.

3. The process of claim 2 wherein the atorvastatin ester derivative is provided as a solute in a $C_1$–$C_4$ alcohol of formula $R_2$—OH wherein $R_2$ is a $C_1$–$C_4$ alkyl group selected independently of $R_1$, and wherein the second atorvastatin ester derivative is of the formula:

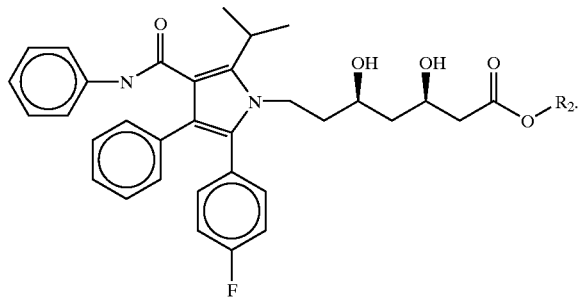

4. The process of claim 2 further comprising recovering the atorvastatin hemi-calcium substantially free of atorvastatin ester derivatives.

5. The process of claim 2 wherein the second atorvastatin ester derivative is converted into atorvastatin hemi-calcium with the calcium hydroxide.

6. The process of claim 1 wherein the mixture further comprises atorvastatin free acid in an amount of less than about 10% with respect to the atorvastatin ester derivative and is converted into atorvastatin hemi-calcium with the calcium hydroxide.

7. The process of claim 1 wherein the calcium hydroxide is a molar excess of calcium hydroxide with respect to the atorvastatin ester derivative.

8. The process of claim 7 wherein the molar excess is greater than about 0.75 and less than about 6 molar equivalents with respect to the atorvastatin ester derivative.

9. The process of claim 8 wherein the converting comprises adding the atorvastatin ester derivative to a mixed solvent comprising about 5% to about 20% water in $C_1$–$C_4$ alcohol and suspending the calcium hydroxide in the mixed solvent.

10. The process of claim 9 wherein from about 10 mmole to about 1 mole of atorvastatin ester derivative per liter of mixed solvent is added.

11. The process of claim 9 wherein the converting further comprises adding a phase transfer agent to the mixed solvent.

12. The process of claim 11 wherein the phase transfer agent is selected from the group consisting of tetra-n-butylammonium bromide, benzyltriethylammonium chloride, tetra-n-butylammonium chloride, tetra-n-butylammonium bromide, tetra-n-butylammonium iodide, tetra-ethylammonium chloride, benzyltributylammonium chloride, benzyltributylammonium bromide, benzyltriethylammonium bromide, tetramethylammonium chloride and polyethylene glycol.

13. A process for preparing atorvastatin hemi-calcium comprising the steps of:
   a) mixing an atorvastatin ester derivative, phase transfer catalyst, and from about 0.75 to about 6 equivalents of calcium hydroxide with respect to the atorvastatin ester derivative in a mixed solvent comprising from about 5% to about 20% water in a $C_1$–$C_4$ alcohol,
   b) heating the mixture to from 50° C. to 70° C. for a period of time sufficient to hydrolyze the atorvastatin ester derivative,
   c) filtering the mixture to remove excess calcium hydroxide,
   d) adding water to the filtrate to precipitate atorvastatin hemi-calcium, and
   e) separating atorvastatin hemi-calcium from the filtrate.

14. A process for preparing atorvastatin hemi-calcium or solvate thereof comprising the steps of:

a) forming a solution of an atorvastatin ester derivative selected from the group consisting of:

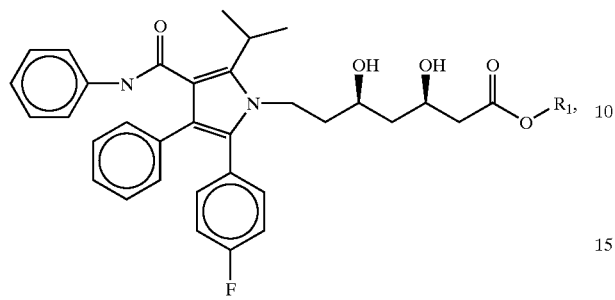

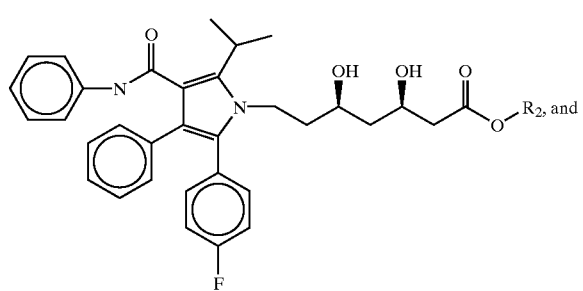

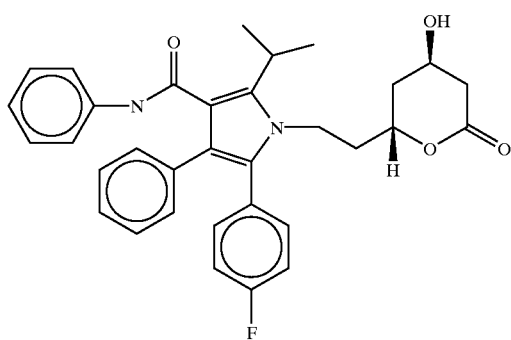

wherein $R_1$ and $R_2$ are each a $C_1$–$C_4$ alkyl group, by converting a dioxane of formula:

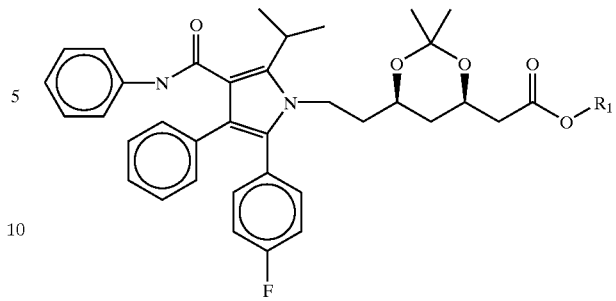

to the atorvastatin ester derivative with an acid catalyst in a mixture of water and a $C_1$–$C_4$ alcohol of formula $R_2$—OH, b) adding calcium hydroxide to the solution to convert the atorvastatin ester derivative to atorvastatin hemi-calcium, and c) recovering the atorvastatin hemi-calcium or solvate thereof from the solution.

15. The process of claim 14 wherein the $C_1$–$C_4$ alcohol and water mixture has a pH of less than about 1, the acid catalyst is hydrochloric acid and $R_2$ is ethyl.

16. The process of claim 14 further comprising evaporating acetone liberated by the conversion of the dioxane to the atorvastatin ester derivative.

17. The process of claim 16 wherein the acetone is evaporated under reduced pressure.

18. The process of claim 14 wherein the calcium hydroxide is a molar excess of calcium hydroxide relative to the dioxane.

19. The process of claim 18 wherein the molar excess is from about 1.5 to about 6 molar equivalents.

20. The process of claim 18 wherein the excess portion of the calcium hydroxide is filtered from the solution before recovering the atorvastatin hemi-calcium or solvate thereof.

21. The process of claim 20 wherein the atorvastatin hemi-calcium or solvate thereof is recovered by precipitation and removal of the $C_1$–$C_4$ alcohol and any dissolved substances.

22. The process of claim 21 wherein the atorvastatin hemi-calcium is caused to precipitate by slow addition of water.

* * * * *